US007629329B2

(12) United States Patent
Lee et al.

(10) Patent No.: US 7,629,329 B2
(45) Date of Patent: Dec. 8, 2009

(54) METHOD FOR INCREASING MUSCLE MASS AND STRENGTH THROUGH ADMINISTRATION OF ADENOSINE TRIPHOSPHATE

(75) Inventors: Steve S. Lee, Sandy, UT (US); Richard B. Hynson, Missoula, MT (US); Joe Zhou, Shanghai (CN)

(73) Assignee: TSI Health Sciences, Inc., Missoula, MT (US)

( * ) Notice: Subject to any disclaimer, the term of this patent is extended or adjusted under 35 U.S.C. 154(b) by 499 days.

(21) Appl. No.: 11/069,746

(22) Filed: Feb. 28, 2005

(65) Prior Publication Data

US 2005/0261238 A1    Nov. 24, 2005

Related U.S. Application Data

(63) Continuation-in-part of application No. 10/162,143, filed on Jun. 3, 2002, now abandoned.

(60) Provisional application No. 60/549,181, filed on Mar. 2, 2004, provisional application No. 60/295,705, filed on Jun. 4, 2001.

(51) Int. Cl.
  *A01N 43/04*     (2006.01)
  *A61K 31/70*     (2006.01)
(52) U.S. Cl. ...................................................... 514/47
(58) Field of Classification Search ........................ None
  See application file for complete search history.

(56) References Cited

U.S. PATENT DOCUMENTS

| | | | |
|---|---|---|---|
| 3,819,830 A | 6/1974 | Yoshimura | |
| 4,880,918 A | 11/1989 | Rapaport | |
| 4,923,851 A | 5/1990 | Carniglia | |
| 5,017,564 A * | 5/1991 | Makino et al. | ................ 514/47 |
| 5,023,244 A | 6/1991 | Goto et al. | |
| 5,030,623 A | 7/1991 | Gruber | |
| 5,049,372 A | 9/1991 | Rapaport | |
| 5,055,304 A * | 10/1991 | Makino et al. | ............... 424/465 |
| 5,227,371 A | 7/1993 | Rapaport | |
| 5,332,579 A | 7/1994 | Umbdenstock | |
| 5,391,550 A | 2/1995 | Carniglia et al. | |
| 5,547,942 A * | 8/1996 | Rapaport | .................... 514/47 |
| 5,616,564 A | 4/1997 | Rapaport et al. | |
| 5,707,971 A | 1/1998 | Fahy | |
| 5,767,159 A | 6/1998 | Hultman et al. | |
| 5,981,601 A | 11/1999 | Nagley et al. | |
| 6,100,287 A | 8/2000 | Stevens et al. | |
| 6,143,784 A | 11/2000 | Greenhaff et al. | |
| 6,159,942 A | 12/2000 | St. Cyr et al. | |
| 6,159,943 A | 12/2000 | Butler et al. | |
| 6,184,214 B1 | 2/2001 | Dogadina et al. | |
| 6,296,892 B1 | 10/2001 | Elseviers et al. | |
| 6,299,857 B1 | 10/2001 | Elmaleh et al. | |
| 6,335,436 B1 | 1/2002 | Rapaport et al. | |
| 6,399,661 B1 | 6/2002 | Golini | |
| 6,429,198 B1 | 8/2002 | St. Cyr et al. | |
| 6,440,660 B1 | 8/2002 | Barker, Jr. et al. | |
| 6,525,027 B2 * | 2/2003 | Vazquez et al. | ................ 514/23 |
| 6,723,737 B1 | 4/2004 | Rapaport | |
| 7,056,529 B2 * | 6/2006 | Ehringer et al. | ............. 424/450 |
| 2002/0052336 A1 | 5/2002 | Yerxa et al. | |
| 2002/0072501 A1 | 6/2002 | Cyr et al. | |

FOREIGN PATENT DOCUMENTS

| | | | |
|---|---|---|---|
| CN | 1234234 | * | 11/1999 |
| WO | WO 97/25972 | | 7/1997 |
| WO | WO 98/34593 | | 8/1998 |
| WO | WO 00/25758 | | 5/2000 |
| WO | WO 01/28528 | * | 4/2001 |
| WO | WO 01/45691 | | 6/2001 |

OTHER PUBLICATIONS

"More Strength..", product flyer for Adenergy with Peak ATP, Jan. 2004.*

Prodcut Description for "Adenergy with Peak ATP" from the website: www.bodyconcept.com/family/1339/display.html.*

Mary L. Ellsworth, "Red Blood Cell-Derived ATP as a Regulator of Skeletal Muscle Perfusion," Medicine and Science in Sports and Exercise, 2004, pp. 35-41.

Kim Schoenhals, "Cognitive Function", Natural Products Industry Insider, Feb. 2, 2004, pp. 18-25.

(Continued)

*Primary Examiner*—Traviss C McIntosh, III
(74) *Attorney, Agent, or Firm*—Marshall, Gerstein & Borun LLP

(57) ABSTRACT

The present invention is directed to compositions having an effective amount of Adenosine Triphosphate ("ATP") sufficient to effect intracellular and extracellular concentrations of ATP in a mammal to improve anaerobic exercise capacity by increasing muscle size and/or strength and methods for using the same. Preferably, a gastric acid secretion inhibitory coating is applied to the effective amount of ATP in a manner that protects the ATP from degradation by gastric juices. ATP compositions of the present invention may be administered in nutraceutical or functional food dosage forms, including oral and non-oral delivery forms. In addition, the effective amount of ATP maybe combined with amino acids, botanicals, functional foods, herbals, nucleotides, nutraceuticals, nutrients, pharmaceuticals, proteins, and/or vitamins in an effort to enhance the targeted activity of the composition.

27 Claims, 18 Drawing Sheets

OTHER PUBLICATIONS

"More Strength, More Energy, More Lean Muscle," product advertisement for optimumnutrition.com regarding ADENERGY™ with Peak ATP™, Jan. 2004.

Pieter C. Dagnelie et al., "Promising Effects of Adenosine Triphosphate Infusion on Nutritional Status and Quality of Life in Advanced Non-Small-Cell Lung Cancer: a Randomized Clinical Trial," *Drug Development Research*, 2003, 59:146-151.

Randy S. Sprague et al., "Extracellular ATP Signaling in the Rabbit Lung: Erythrocytes as Determinants of Vascular Resistance," *Am J. Phvsiol Heart Circ Physiol*, 2003, 285: H693-H700.

Hendrik J. Agteresch, et al., "Beneficial Effects of Adenosine Triphosphate on Nutritional Status in Advanced Lung Cancer Patients: A Randomized Clinical Trial, " *Journal of Clinical Oncology*, vol. 20, No. 2, Jan. 15, 2002, pp. 371-378.

Josè Gonzàlez-Alonso et al., "Erythrocyte and the Regulation of Human Skeletal Muscle Blood Flow and Oxygen Delivery," *Circulation Research*, Nov. 29, 2002, pp. 1046-1055.

Susanne Leij-Halfwerk, et al., "Adenosine Triphosphate Infusion Increases Liver Energy Status in Advanced Lung Cancer Patients: An In Vivo 31P Magnetic Resonance Spectroscopy Study," *Hepatology*, Feb. 2002, pp. 421-423.

H. J. Agteresch et al., "Pharmacokinetics of Intravenous ATP in Cancer Patients", *Eur J. Clin Pharmacol*, (2000) vol. 56, pp. 49-55.

Ketty Kichenin et al., "Chronic Oral Administration of ATP Modulates Nucleoside Transport and Purine Metabolism in Rats," *The Journal of Pharmacology and Experimental Therapeutics* (U.S.A. 2000), vol. 294, No. 1, pp. 126-133.

Ketty Kichenin, et al., "Cardiovascular and Pulmonary Response to Oral Administration of ATP in Rabbits," *J. Appl. Pysiol*, 2000, pp. 1962-1968.

Kato M, et al., "Adenosine 5'—Triphosphate Induced Dilation of Human Coronary Microvessels in Vivo," *Intern Med.* 1999, vol. 38, No. 4, pp. 324-329.

Arakawa A, et al., "Preparation of Liposome-Encapsulating Adenosine Triphosphate," *Tohoku J Exp. Med.* Jan. 1998, vol. 184, No. 1, pp. 39-47.

Maresh CM, et al., "Dietary Supplementation and Improved Anaerobic Performance," *International Journal of Sport Nutrition* Dec. 1994; vol. 4, No. 4, pp. 387-397.

GX Xu, et al., "Studies on the Preparation of Adenosine Triphosphate (ATP) Liposomes" 1989, vol. 24, No. 2, pp. 133-138.

T. Forrester et al., "Effect of Adenosine Triphosphate and Some Derivatives on Cerebral Blood Flow and Metabolism", *J. Physiol.* (1979), vol. 296, pp. 343-355.

"Intestinal Absorption of Adenosine Triphosphate," *Nutritional Reviews*, vol. 36, No. 10, Oct. 1978, pp. 309-311.

Kono H, et al., "Intestinal Absorption of ATP in Healthy Subjects," *Naika* 1971, vol. 28, No. 5, pp. 943-945.

Myron H. Steinberg, "Adenosine-5-Monophosphate in Venous Insufficiency," *Angiology*, 1958; 9:154-161.

Raymond Boller et al., "Therapeutic Action of Muscle Adenylic Acid on Ulcers and Dermatitis Associated with Varicose or Phlebitic Veins; Follow Up Report," *Angiology*, 1952, 3: 260-266.

John W. Daly, "Adenosine Receptors: Targets for Future Drugs," Journal of Medicinal Chemistry, vol. 25, No. 3, Mar. 1982, pp. 197-207.

* cited by examiner

TABLE 1. Data represent total plasma ATP (μM) and blood ATP (mmols/Hct) parameters for 27 subjects receiving high dose ATP (225 mg), low dose ATP (150 mg), or placebo treatment.

| | | | Plasma (ATP μM) and Blood (ATP mmols/Hct) | | | | | |
|---|---|---|---|---|---|---|---|---|
| | | | Acute Dosing (Pre-Ingestion) | | Acute Dosing (Post-Ingestion) | | Post | |
| Group | N | Hct (%) | Plasma | Blood | Plasma | Blood | Plasma | Blood |
| High | 9 | 42.03 (2.0) | 0.21 (0.1) | 1.79 (0.3) | 0.19 (0.1) | 1.98 (0.1) | 0.26 (0.1) | 1.76 (0.3) |
| Low | 9 | 41.63 (2.1) | 0.20 (0.1) | 1.77 (0.2) | 0.23 (0.1) | 1.94 (0.3) | 0.26 (0.4) | 1.72 (0.2) |
| Placebo | 9 | 42.24 (2.8) | 0.19 (0.1) | 1.74 (0.2) | 0.21 (0.2) | 1.80 (0.5) | 0.22 (0.1) | 1.63 (0.1) |

Hct (%), percentage of hemocrit.
Variables expressed as mean (SE).
Post refers to that testing period following 14 days of supplementation.

FIG. 11

TABLE 2. Data represent Wingate performance and blood lactic acid concentration for 27 subjects receiving high dose ATP (225 mg), low dose ATP (150 mg), or placebo treatment.
Variables expressed as mean (SE).
Post refers to that testing period following 14 days of supplementation.

| | | Wingate Test 1 | | | Wingate Test 2 | | |
|---|---|---|---|---|---|---|---|
| | Group | Baseline | Acute Dosing | Post | Baseline | Acute Dosing | Post |
| Total Work (KJ) | High | 23.39 (3.0) | 23.72 (2.0) | 22.92 (2.0) | 22.42 (3.0) | 20.99 (2.0) | 19.86 (3.0) |
| | Low | 24.45 (2.5) | 23.44 (2.0) | 24.27 (2.5) | 22.18 (3.0) | 20.99 (4.0) | 21.36 (3.0) |
| | Placebo | 25.12 (3.0) | 24.46 (3.0) | 24.45 (2.0) | 22.76 (4.0) | 21.76 (4.0) | 21.79 (3.0) |
| Average PO (Watts) | High | 779.70 (36.9) | 790.55 (26.7) | 763.96 (26.0) | 747.43 (34.7) | 699.77 (24.9) | 661.93 (27.6) |
| | Low | 814.85 (29.8) | 781.22 (31.6) | 808.95 (35.8) | 739.32 (34.6) | 712.64 (27.3) | 712.06 (26.9) |
| | Placebo | 837.38 (35.8) | 815.50 (29.1) | 814.94 (26.5) | 758.60 (48.5) | 725.48 (46.7) | 726.44 (37.4) |
| Peak PO (Watts) | High | 1550.22 (102.5) | 1569.89 (51.5) | 1417.00 (56.7) | 1495.11 (57.7) | 1415.22 (60.3) | 1434.44 (59.7) |
| | Low | 1511.11 (55.5) | 1462.67 (42.3) | 1473.56 (21.8) | 1421.78 (25.5) | 1407.67 (45.1) | 1428.44 (23.3) |
| | Placebo | 1577.11 (57.8) | 1543.44 (30.6) | 1481.78 (26.8) | 1488.56 (56.1) | 1487.67 (77.1) | 1430.78 (24.9) |
| Post Wingate Lactate (mmol/L) | High | 7.86 (0.7) | 7.72 (0.5) | 8.47 (0.5) | 10.09 (0.8) | 9.90 (0.5) | 11.03 (0.6) |
| | Low | 9.07 (0.4) | 9.16 (0.7) | 9.49 (0.9) | 11.61 (0.6) | 10.78 (0.7) | 11.27 (0.9) |
| | Placebo | 17.57 (9.4) | 8.26 (0.7) | 8.93 (0.8) | 10.61 (0.6) | 10.26 (0.4) | 10.91 (0.8) |

FIG. 12

TABLE 3. Data represent 1-RM bench press and strength indices for 27 subjects receiving high dose ATP (225 mg), low dose ATP (150 mg), or placebo treatment.

|  | Group | Baseline | Acute Dosing | Post |
|---|---|---|---|---|
| 1-RM (kg) | High | 123.03 (20.9) | 131.16 *(24.6) | 129.60(25.9) |
|  | Low | 114.80 (9.1) | 119.35 (35.0) | 119.35 (35.0) |
|  | Placebo | 118.99 (22.7) | 120.91 (19.1) | 116.92 (18.2) |
| 70% 1-RM (kg) | High | 86.06 (15.5) | 93.59 (17.3) | 91.51 (18.2) |
|  | Low | 80.91 (24.5) | 83.54 (24.5) | 83.54 (24.5) |
|  | Placebo | 83.94 (15.0) | 85.20 (13.6) | 82.07 (13.2) |
| Set 1 repetitions | High | 13.77(4.0) | 14.89 (4.0) | 16.32† (3.0) |
|  | Low | 13.55 (4.0) | 13.44 (4.0) | 13.86 (5.0) |
|  | Placebo | 14.94 (4.0) | 15.00 (4.0) | 15.88 (3.0) |
| Set 2 repetitions | High | 9.44 (3.0) | 7.99 (2.0) | 8.12 (1.0) |
|  | Low | 6.99 (2.0) | 7.26 (3.0) | 7.22 (3.0) |
|  | Placebo | 6.67 (3.0) | 6.23 (3.0) | 6.87 (2.0) |
| Set 3 repetitions | High | 6.34 (3.0) | 5.99 (2.0) | 6.12 (2.0) |
|  | Low | 4.77 (2.0) | 4.22 (2.0) | 4.66 (2.0) |
|  | Placebo | 4.44 (2.0) | 4.43 (2.0) | 4.99 (2.0) |
| Total Lifting Volume (kg) | High | 2497.02 (220.9) | 2350.76 (278.0) | 3201.06 † (184.3) |
|  | Low | 2025.40 (242.1) | 2131.11 (309.6) | 2544.24 (357.7) |
|  | Placebo | 2174.09 (216.5) | 2182.32 (250.4) | 2603.54 (218.1) |

*P < 0.05 vs. baseline, †P < 0.01 vs. baseline.

Variables expressed as mean (SE).
Post refers to that testing period following 14 days of supplementation.

FIG. 13

Table 4. Data represent individual and group mean change data for 1-RM bench press testing. Each value is compared to baseline and presented in kg.

| Subject | Group | Acute | Post |
|---|---|---|---|
| Sub 1 | High | 6.8 | 6.8 |
| Sub 2 | High | 21.4 | 21.4 |
| Sub 3 | High | 6.8 | 6.8 |
| Sub 4 | High | 0.0 | 0.0 |
| Sub 5 | High | 0.0 | 0.0 |
| Sub 6 | High | 0.0 | 0.0 |
| Sub 7 | High | 28.6 | 28.6 |
| Sub 8 | High | 0.0 | 0.0 |
| Sub 9 | High | 7.3 | 7.3 |
| | Mean | 7.9 | 7.9 |
| | SEM | 3.5 | 3.5 |
| Sub 10 | Low | 0.0 | 0.0 |
| Sub 11 | Low | 0.0 | 0.0 |
| Sub 12 | Low | 7.3 | 0.0 |
| Sub 13 | Low | 7.3 | 0.0 |
| Sub 14 | Low | 6.8 | 0.0 |
| Sub 15 | Low | 21.4 | 0.0 |
| Sub 16 | Low | 0.0 | 0.0 |
| Sub 17 | Low | 0.0 | 0.0 |
| Sub 18 | Low | 0.0 | 0.0 |
| | Mean | 4.7 | 0.0 |
| | SEM | 2.4 | 0.0 |
| Sub 19 | Placebo | 0.0 | 0.0 |
| Sub 20 | Placebo | 0.0 | -7.3 |
| Sub 21 | Placebo | 6.8 | 0.0 |
| Sub 22 | Placebo | 7.3 | 0.0 |
| Sub 23 | Placebo | 0.0 | 0.0 |
| Sub 24 | Placebo | 6.8 | 0.0 |
| Sub 25 | Placebo | -7.3 | -21.4 |
| Sub 26 | Placebo | 0.0 | 0.0 |
| Sub 27 | Placebo | 14.5 | -7.3 |
| | Mean | 3.2 | -1.6 |
| | SEM | 2.1 | 1.1 |

FIG. 14

METHOD FOR INCREASING MUSCLE MASS AND STRENGTH THROUGH ADMINISTRATION OF ADENOSINE TRIPHOSPHATE

RELATED APPLICATION

This application claims the benefit of U.S. Provisional Patent Application Ser. No. 60/549,181, filed Mar. 2, 2004, and entitled "METHOD FOR INCREASING MUSCLE MASS AND STRENGTH THROUGH ADMINISTRATION OF ADENOSINE TRIPHOSPHATE," and is a continuation-in-part of U.S. patent application Ser. No. 10/162,143, filed Jun. 3,2002, now abandoned and entitled "METHOD FOR INCREASING HUMAN PERFORMANCE BY REDUCING MUSCLE FATIGUE AND RECOVERY TIME THROUGH ORAL ADMINISTRATION OF ADENOSINE TRIPHOSPHATE," which claims priority to U.S. Provisional Patent Application Ser. No. 60/295,705, filed Jun. 4, 2001, and entitled "METHOD FOR INCREASING HUMAN PERFORMANCE BY REDUCING MUSCLE FATIGUE AND RECOVERY TIME THROUGH ORAL ADMINISTRATION OF ADENOSINE TRIPHOSPHATE," all of which are incorporated herein by reference.

BACKGROUND

1. Field of the Invention

This invention relates to the use of adenosine triphosphate (ATP) and, more particularly, to novel systems and methods for administration of ATP for the enhancement of muscle mass and/or strength.

2. The Background

The biological importance of adenosine triphosphate (ATP) first became apparent with the discovery of ATP in muscle tissue infusions by Fiske and Lohmann et al. in 1929. A. Szent-Gyorgi took the next logical step by demonstrating that ATP played an important role in muscle contraction. His experiments involved the addition of ATP to muscle fibers and then observing the subsequent contractions. Various researchers and those skilled in the art have progressively elucidated the role of ATP in muscle function since then. From these beginnings came the understanding and appreciation that ATP is the essential energy production molecule for every cell in the body. Similar phosphate-rich compounds are also found in every organism with ATP related compounds supplying all cellular energy. In 1982, Chaudry at the Yale Medical School published results showing that ATP was present in intracellular and interstitial fluids, thereby suggesting ATP's greatly expanded biological importance.

ATP and its breakdown product adenosine are also inherently involved in a number of extracellular processes like that of muscle contraction as described above. For example, some of the extracellular processes involving ATP may include neurotransmission, cardiac function (e.g., cardiac output, stroke volume, heart rate), platelet function, vasodilatation, perfusion (e.g., arterial pressure, cardiac output, total peripheral resistance), and liver glycogen metabolism.

As can be appreciated, these additional biological roles have given rise to various clinical applications of ATP and adenosine. For example, clinical applications may include applications of ATP and adenosine as aneuropathic and ischemic anaesthesia, ahypotensive agent for trauma or disease induced hypertension such as pulmonary hypertension, a mild hypoglycemic in type II diabetes, and at least preliminary evidence that ATP may be useful as an adjunctive therapy for radiation cancer treatment.

ATP and related compounds have been researched extensively for possible drug uses (see, Daly, J. Med. Chem., 25:197, (1982)). The most widespread of these clinical applications is in various cardiac treatments including the prevention of reperfusion injury after cardiac ischemia or stroke, the treatment of hypertension (see, Jacobson, et al., J. Med. Chem., 35, 407-422 (1992)), as well as the treatment of paroxysmal supra ventricular tachycardia (see, Pantely, et al., Circulation, 82, 1854 (1990)).

With regards to human performance specifically, the splitting of ATP to form adenosine diphosphate (ADP) is of critical importance in the functioning of muscle, since this is the reaction that directly supplies energy to myosin and actin to facilitate normal muscular contraction. In many cases, this requirement is met by the actual rebuilding of ATP as it is used, rather than by storing a very large amount of ATP in the muscle. However, under exceptionally demanding conditions, such as peak athletic performance or certain deficiency states induced by either inadequate nutrition or various diseases, ATP availability could prove to be a limiting step in actuating peak muscle output.

While therapeutic uses of ATP in various disease states is quite common, applications of ATP relating to possible benefits such as increased athletic performance in normal, healthy individuals appear to be largely absent in the published literature.

A method of increasing intracellular ATP through orally administered precursors of adenosine triphosphate in dietary supplements for treatment of reduced energy availability resulting from strenuous physical activity, illness, or trauma appears to be disclosed in U.S. Pat. No. 6,159,942. However, ATP itself is not administered; rather pentose sugars are administered individually, mixed into dry food or in solution. Specifically, the preferred pentose is D-ribose, singly or combined with creatine, pyruvate, L-carnitine, and/or vasodilating agents.

As appreciated by those skilled in the art, the mechanism of action for ribose to stimulate ATP production is through the phosphorylation of nucleotide precursors that may be present in the tissues. These are converted to adenosine monophosphate (AMP) and further phosphorylated to ATP. Adenosine is directly phosphorylated to AMP, while xanthine and inosine are first ribosylated by 5-phosphoribosyl-1-pyrophosphate (PRPP) and then converted to AMP. In the de novo synthetic pathway, ribose is phosphorylated to PRPP, and condensed with adenine to form the intermediate AMP. AMP is further phosphorylated via high energy bonds to form adenosine diphosphate (ADP) and ATP.

In certain circumstances, ATP can cross directly into the cell without the need for intracellular de novo synthesis. Chaudry (1982) explained that exogenous ATP crosses cellular membranes when depletion occurs within myosin units. ATP or ATP substrates may access human physiology orally, sublingually, or intravenously. Carbohydrates, oral ATP, or oral-sublingual ATP may be consumed for enhancing endurance performance and for preventing muscle exertion or heat stress cramps. Therefore, methods of delivering actual ATP to the bloodstream and subsequently to interstitial fluids may have benefits not associated with mere ATP precursors.

In addition to exhibiting the proper therapeutic effect, any method for delivering actual ATP to muscle cells in an attempt to prevent depletion must also include a consideration of the realities of the practical administration of a therapeutic agent in a daily athletic environment. First, the therapeutic agent must be suitable for sale as a dietary supplement, and/or functional food and not only as a drug. This requires that the therapeutic agent have certain technical and economic characteristics related to the dietary supplement and/or functional food industries. From a technical standpoint, the therapeutic agent should preferably be orally administered and suitable for inclusion in a variety of dosage forms such as tablets or capsules or may be included in-solid foods mixed into dry food or in solution. Additionally, the therapeutic agent should also be well tolerated vis a vis digestion and suitably stable both ex vivo and in vivo. From an economic standpoint, a therapeutic agent should ideally be robust enough for combination with a variety of other ingredients without the need for special handling during manufacture or special processing, packaging, or storing of the resulting composition or mixture.

ATP is generally known to be subject to degradation from exposure to high temperature and/or high humidity conditions and in the presence of a low pH, such as that found in stomach acid. It is therefore desirable to protect administered ATP from degradation by stomach acid through the use of a low. pH insoluble compound, such as a protective enteric coating. Sublingual ATP preparations, which are not generally subject to exposure to gastric fluids, exist but they are not typically suitable for inclusion in a variety of dosage forms and complex formulations. This creates the need to coat supplements containing currently available ATP (such as adenosine-5'-triphosphate disodium) to impart protective enteric properties after the final dosage form is manufactured.

While the technique of enteric coating has been applied to finished ATP dosage forms such as capsules and tablets, it has not been applied to bulk ATP preparations suitable for inclusion in alternate dosage forms common to nutritional supplements and/or functional food products such as liquids, nutrition bars, and powders, as well as, the above-mentioned tablets and capsules.

Consistent with the foregoing, an ideal ATP preparation should include protective enteric properties independent of the final dosage form, thus eliminating the need for potential customers to impart enteric protection during manufacture since this capability is both expensive and uncommon. And, additionally providing enteric protection for finished food dosage forms such as liquids, bars, and powders is not presently possible.

SUMMARY AND OBJECTS OF THE INVENTION

In view of the foregoing, it is a primary object of the present invention to provide novel systems and methods for increasing muscle mass and/or strength through administration of adenosine triphosphate (ATP).

In addition, it is an object of the present invention to provide novel systems and methods for delivering and/or administration of ATP in a manner that protects the ATP from degradation by gastric juices through enteric coating to enhance absorption into the blood stream and provide additional therapeutic benefit when compared with non-protected forms of ATP.

It is also an object of the present invention to provide novel systems and methods for coating ATP for enteric administration that are compatible with manufacture of foods, drugs, and dietary supplements of complex formulation and various dosage forms including capsules, tablets, caplets, lozenges, liquids, sublingual, solid foods, powders, and other conceivable dosage forms, as applicable, without the need for imparting enteric properties to the entire mixture, any other part of the mixture, or finished products.

It is a further object of the present invention to provide novel systems and methods for increasing muscle mass and/or strength through delivery and/or administration of ATP using any pharmaceutical delivery form, for example and not by way of limitation, tablet, capsule, powder, granule, microgranule, pellet, soft-gel, controlled-release form, liquid, solution, elixir, syrup, suspension, emulsion, magma, gel, cream, ointment, lotion, transdermal, sublingual, ophthalmic form, nasal form, otic form, aerosol, inhalation form, spray, parenteral form (e.g., intravenous, intramuscular, subcutaneous), suppository, and the like.

It is a still further object of the present invention to provide novel systems and methods for increasing muscle mass and/or strength through delivery and/or administration of ATP using any nutraceutical delivery form, for example and not by way of limitation, tablet, capsule, powder, granule, microgranule, pellet, soft-gel, controlled-release form, liquid, solution, elixir, syrup, suspension, emulsion, magma, gel, cream, ointment, lotion, transdermal, sublingual, ophthalmic form, nasal form, otic form, aerosol, inhalation form, spray, parenteral form (e.g., intravenous, intramuscular, subcutaneous), suppository, and the like.

In addition, it is an object of the present invention to provide novel systems and methods for increasing muscle mass and/or strength through delivery and/or administration of ATP using any functional food delivery form, for example and not by way of limitation, bar, beverage, bread, cereal, cracker, egg, juice and juice drink, milk and soft cheese, mineral water, pasta, pasta sauce, probiotic drink soya product, spread, stimulation/energy beverage, yogurt, baby and/or children's food, women's product, men's product, meal replacement, and the like.

Also, it is an object of the present invention to provide novel systems and methods for increasing muscle mass and/or strength through delivery and/or administration of ATP which may be used in combination with other amino acids, botanicals, functional foods, herbals, nucleotides, nutraceuticals, nutrients, pharmaceuticals, proteins, vitamins, and/or the like.

It is a further object of the present invention to provide novel systems and methods for increasing organ perfusion and/or organ function through delivery and/or administration of an effective amount of ATP, alone or in combination with other amino acids, botanicals, functional foods, herbals, nucleotides, nutraceuticals, nutrients, pharmaceuticals, proteins, vitamins, and/or the like.

It is a still further object of the present invention to provide novel systems and methods for reducing pain perception by inhibiting sensory nerves and/or nociceptors through administration of an effective amount of ATP, alone or in combination with other amino acids, botanicals, functional foods, herbals, nucleotides, nutraceuticals, nutrients, pharmaceuticals, proteins, vitamins, and/or the like.

Also, it is an object of the present invention to provide novel systems and methods for increasing cognitive function and/or promoting a sense of well-being through delivery and/or administration of an effective amount of ATP, alone or in combination with other amino acids, botanicals, functional foods, herbals, nucleotides, nutraceuticals, nutrients, pharmaceuticals, proteins, vitamins, and/or the like.

Consistent with the foregoing objects, the present invention provides systems and methods for delivering and/or administering an effective amount of ATP for increasing muscle mass and/or muscle strength. Said systems and methods may deliver and/or administer ATP in a manner that protects the ATP from degradation by gastric juices through enteric coating to enhance absorption into the blood stream and provide additional therapeutic benefit when compared with non-protected forms of ATP. In addition, said systems and methods may deliver and/or administer an effective amount of ATP for enhancing organ perfusion, enhancing organ function, reducing the pain perception (i. e., anti-nociceptor function), and/or promoting an enhanced sense of well-being. In preferred embodiments of the present invention, a gastric acid secretion inhibitory coating may be applied to the effective amount of ATP in a manner that protects the ATP from degradation by gastric juices. As contemplated herein, the effective amount of ATP may be delivered by means of any conventional pharmaceutical, nutraceutical, or functional food delivery form.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 11 is a table illustrating an example of one presently preferred embodiment of total plasma and blood ATP parameters for twenty-seven (27) study participants receiving high dose ATP (i.e., 225 mg), low dose ATP (i.e, 150 mg), or placebo treatment;

FIG. 12 is a table illustrating an example of one presently preferred embodiment of the results of the Wingate performance tests blood lactic acid concentration;

FIG. 13 is a table summarizing an example of one presently preferred embodiment of the results of the 1-RM bench press and strength indices for twenty-seven (27) study participants receiving high dose ATP (i. e., 225 mg), low dose ATP (i. e, 150 mg), or placebo treatment;

FIG. 14 is a table illustrating an example of one presently preferred embodiment of the change in individual and group mean data for 1-RM bench press testing;

DETAILED DESCRIPTION OF THE PREFERRED EMBODIMENTS

Figure 1:
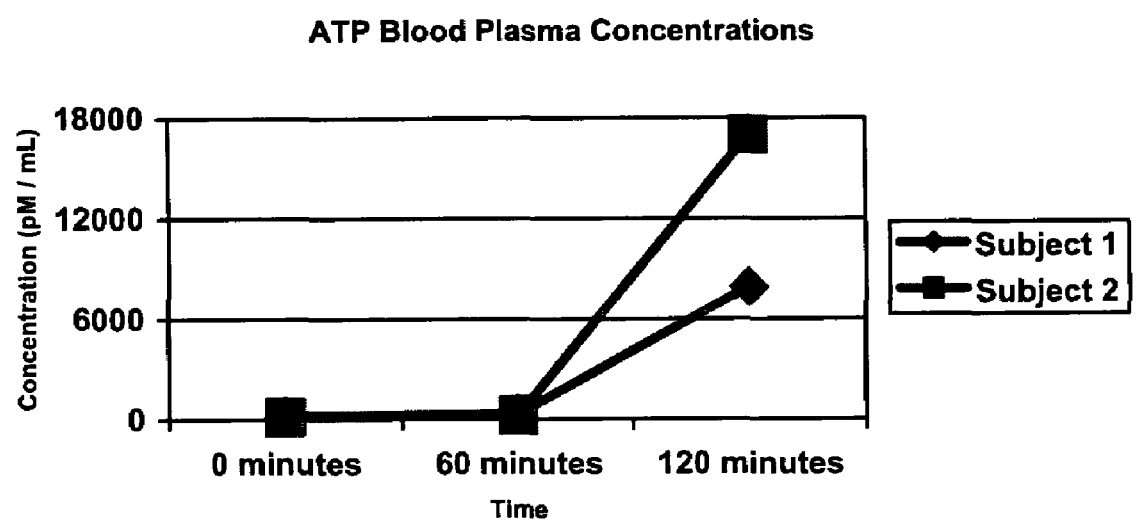
FIG. 1 is a graph illustrating the changes in ATP blood plasma concentrations over 120 minutes following administration of one presently preferred embodiment of an ATP composition of the present invention.

It will be readily understood that the components of the present invention, as generally described and illustrated in the Figures herein, could be modified, arranged and designed in a wide variety of different configurations. Thus, the following more detailed description of the embodiments of the systems and methods of the present invention, as represented in the Examples and FIGS. 1 through 18, is not intended to limit the scope of the invention. The scope of the invention is as broad as claimed herein.

Oral administration of ATP is usually in the form of Adenosine-5'-Triphosphate Disodium. For the purpose of contemplating the breadth and scope of the present invention, Adenosine-5'-Triphosphate Disodium or any form of ATP or adenosine suitable for oral administration may be combined with any of the known coatings suitable for imparting enteric properties in granular form.

Granular formation or agglomeration may be achieved by means of any conventional method including for example, but not by way of limitation, fluidized bed granulation, wet granulation, or spherical rotation agglomeration. Subsequent enteric coatings may include, for example and not by way of limitation, methacrylic acid-acrylic acid copolymers, cellulose acetate phthalate, hydroxypropylmethylcellulose phthalate and acetate succinate, shellac, polyethylene glycol, polysorbates, carboxymethylcellulose or polyoxyethylene-polyoxypropylene glycol. Furthermore, the objects of the present invention may be at least partially accomplished through the use of quasi-enteric coatings or materials such as those which result in delayed or timed release of active ingredients such as sugars, castor oil, microcrystalline cellulose, starches such as maltodextrin or cyclodextrin, or food-grade gums or resins.

A water barrier overcoat may then be applied to assist in isolating the ATP active from other formulation ingredients, as well as to provide protection versus environmental degradation.

In human performance enhancing formulations, the resulting ATP may be incorporated into the delivery and/or administration form in a fashion so as to result in a typical dosage range of about twenty-five (25) mg to about two-hundred and twenty-five (225) mg, though more or less may be desirable depending on the application and other ingredients. In one presently preferred embodiment of the present invention, an effective dosage range may be administered in divided dosages, such as two (2) to three (3) times per day for maximum effectiveness.

For the purposes of establishing definitional support for various terms that are used in the present application, the following technical comments and review are provided:

"Ergogenic" may be defined as the ability to increase capacity for bodily and/or mental labor, especially by reducing or eliminating signs and symptoms of fatigue. "Anaerobic" may be literally defined as without oxygen. "Anaerobic exercise" may be defined as exercise which does not increase the body's requirement for oxygen. Typically, anaerobic exercise may be a short-burst, higher-intensity exercise. Proteins and carbohydrates may be utilized to build muscle mass and/or strength. Fat burning may be an indirect effect of anaerobic exercise. Anaerobic exercise may include, for example and not by way of limitation, push-ups, pull-ups, sit-ups, sprinting, stomach crunches, weight lifting, strength training, and the like.

"Aerobic" may be literally defined as with oxygen. "Aerobic exercise" may be defined as exercise which increases the body's requirement for oxygen. Typically, aerobic exercise involves an increased respiratory (i.e., breathing) rate and cardiac (i.e., heart) rate over an extended period of time. Following approximately twenty (20) minutes of aerobic exercise, the body usually requires the utilization of stored fat deposits as fuel for muscle contraction. Therefore, aerobic exercise may be considered to have a direct fat burning effect. Aerobic exercise may include, for example and not by way of limitation, basketball, bicycling, cross-country skiing, ice hockey, ice skating, jogging, martial arts, rollerblading, rowing, soccer, swimming, tennis, walking (e.g., fast), and the like.

"Bench press" may be defined as a muscular strength test and a method for conducting strength training. Typically, bench press exercises involve at least one repetition of extending weight in a perpendicular direction from the chest while the body is in a supine position.

"Wingate test" may be defined as a cycle ergometer test used to measure muscle work over a relatively short period (e.g., thirty (30) seconds), and may also be used to measure a fatigue index.

"Perfusion" may be defined as the pumping of a fluid through an organ or tissue. Typically, perfusion may be used to describe the volume and/or effectiveness of supplying blood to any one or more of the organs in the body of a human or animal. Perfusion may be used to enhance the function of an organ, for example and not by way of limitation, the brain, liver, heart, lung, kidney, nerve, muscle, intestine, and the like.

The following examples will illustrate the invention in further detail. It will be readily understood that the composition of the present invention, as generally described and illustrated in the Examples herein, could be synthesized in a variety of formulations and dosage forms. Thus, the following more detailed description of the presently preferred embodiments of the methods, formulations, and compositions of the present invention, as represented in Examples I-VIII is not intended to limit the scope of the invention, as claimed, but it is merely representative of the presently preferred embodiments of the invention.

EXAMPLE I

In one presently preferred embodiment of an ATP composition of the present invention, twenty-one (21) mg of Adenosine-5'-Triphosphate Disodium was entabletted in a Stokes B2, sixteen (16) station tablet press using ⅜" standard concave punch dies. The resulting tablets included microcrystalline cellulose as an inert filler and less than three percent (3%) magnesium stearate as a lubricant. Total tablet weight was about 350 mg and the resulting tablet hardness was approximately 12 kp. The tablet cores were then coated with ten percent (10%) methacrylate copolymer (Eudragit from Rohm, Germany).

The resulting tablets comprising one presently preferred embodiment of the ATP composition of the present invention were then given to two (2) healthy male volunteers, ages fifty-one (51) and fifty-seven (57), respectively, for the purpose of evaluating the ability of the present invention to deliver ATP to blood plasma. Referring now to FIG. 1, a graph shows the increase in ATP blood plasma concentration levels from zero (0) to 120 minutes following oral administration of one presently preferred ATP composition of the present invention in the two (2) human subjects.

As these results clearly illustrate, the ATP composition of the present invention results in dramatically increased ATP blood plasma concentrations in a manner consistent with effective enteric delivery.

EXAMPLE II

In one presently preferred embodiment of an ATP composition of the present invention, twenty-five (25) mg of Adenosine-5'-Triphosphate Disodium was entabletted in a Stokes B2, sixteen (16) station tablet press using ⅜" standard concave punch dies. The resulting tablets included microcrystalline cellulose as an inert filler and less than three percent (3%) magnesium stearate as a lubricant. Total tablet weight was about 350 mg and the resulting tablet hardness was approximately 12 kp. The tablet cores were then coated with ten percent (10%) methacrylate copolymer (Eudragit from Rohm, Germany).

The resulting tablets comprising one presently preferred embodiment of the ATP composition of the present invention were then given to twenty-one (21) volunteers for the purpose of evaluating the effectiveness of the ATP composition of the present invention as an aid to enhancing human performance. The study demographics may be summarized as follows:

|  |  | Avg Weight (kg) | Age (years) | Number in Group (n) |
|---|---|---|---|---|
| Control: | Males | 84.5 | 26.1 | 6 |
|  | Females | 63.1 | 30.7 | 4 |
| ATP: | Males | 76.1 | 28.0 | 7 |
|  | Females | 58.0 | 22.4 | 4 |

Doses were given in double blind fashion, wherein neither the recipient nor the researcher was aware of active versus placebo administration. Results were measured using a standard Wingate test for measuring endurance.

As appreciated by those skilled in the art, since the 1970's, the Wingate test has become "one of the most widely recognized protocols in exercise research for determining peak muscle power and indirectly reflecting anaerobic capacity." (See, Roberg and Roberg, Exercise Physiology, Musky Publishers 1997) The test consists of pedaling or arm cranking at maximal effort for 30 seconds against a constant load. The Wingate test may be used to quantify the mean and peak power that are generated during the test. The decline in power that may occur during the Wingate test may be defined as a fatigue index.

The application of the test in the present example specifically sought to measure muscle recovery following the administration of a single Wingate maximal effort test lasting fifteen seconds by contrasting the output with a second Wingate maximal effort test conducted immediately following the first test. The results were measured for a period of 120 minutes with the first pair of tests conducted beginning two hours after administration of the ATP composition of the present invention and then again every thirty minutes thereafter.

Figure 2:
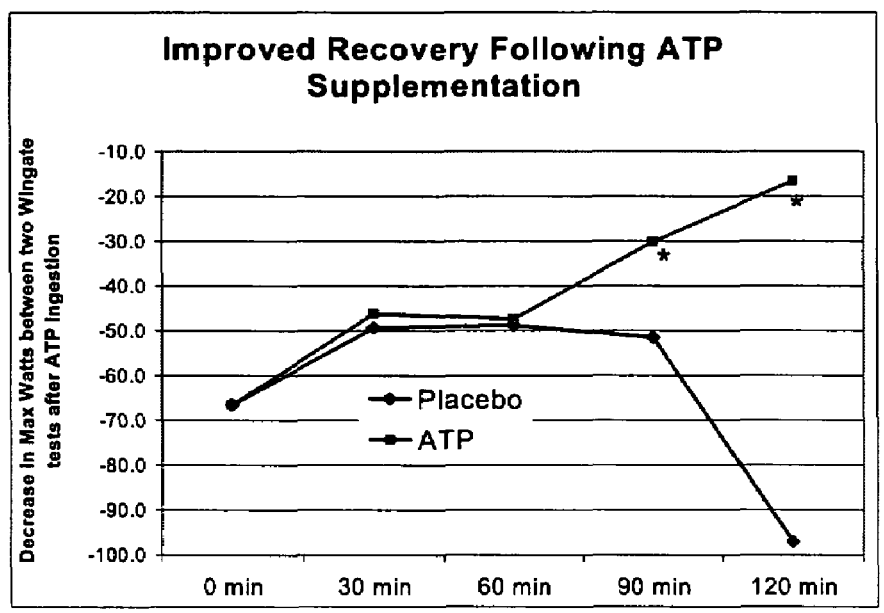
FIG. 2 is a graph illustrating improvements in muscle recovery following. supplementation with one presently preferred embodiment of an ATP composition of the present invention.

Referring now to FIG. 2, the results of the experiment are illustrated in graph form. In particular, the vertical axis may show the decrease in Max Watts between the first and second Wingate tests after ingestion of the ATP composition of the present invention. The horizontal axis may show the change in time between zero (0) and 120 minutes. As shown in FIG. 2, notable differences in muscle recovery may be observed at 90 minutes and 120 minutes following the administration of the ATP composition. These results show significant improved muscle recovery and substantially less depletion of maximal output versus placebo following administration of the ATP composition of the present invention. Moreover, the results of the study also indicate a persistent effect that peaks sometime around or after 120 minutes.

EXAMPLE III

Using the same tablet preparation of one presently preferred embodiment of an ATP composition of the present invention as used in Example II, another series of tests were conducted to evaluate the effects of a single dose (containing about twenty-five (25) mg ATP) of the present invention on various parameters measuring performance using three back-to-back Wingate tests. The first test was administered two hours after oral administration of the tablet prepared in accordance with one presently preferred method of producing an ATP composition of the present invention. Referring generally to FIGS. 3-8, the results of Example III may be illustrated as several different measurements of a series of anaerobic and other exercises tests.

Figure 3:
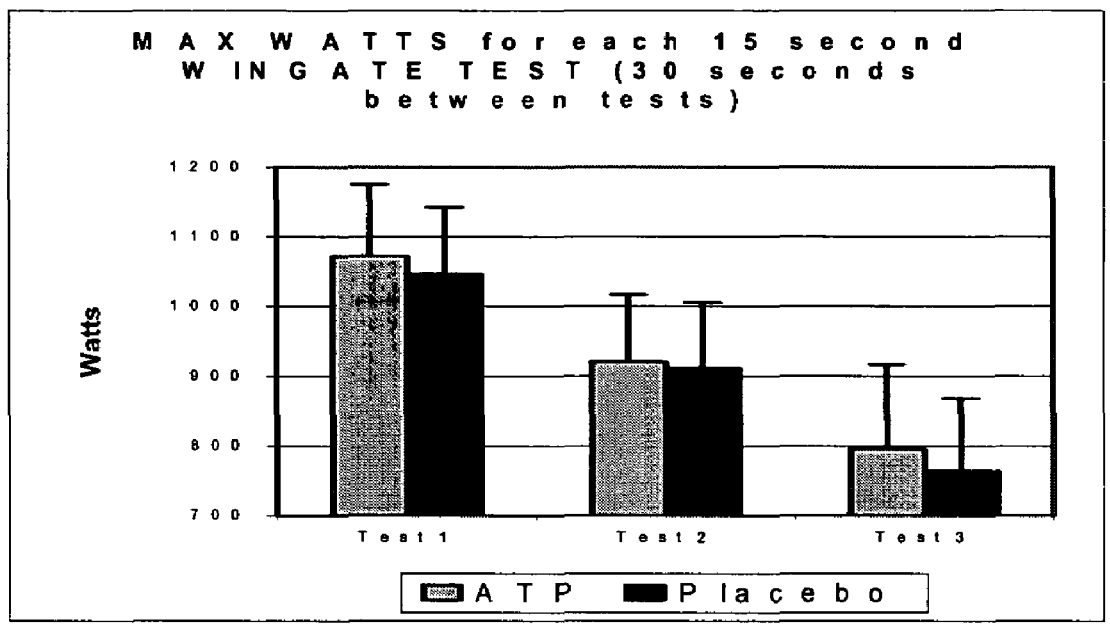
FIG. 3 is a graph illustrating the difference max watts between placebo and one presently preferred embodiment of an ATP composition of the present invention for three (3) successive ergonometric tests.

Referring specifically to FIG. 3, a bar graph illustrates one presently preferred embodiment of a level of maximum muscle output during the entire 15 second test for each of the three back-to-back tests following administration of the ATP composition of the present invention versus placebo.

Figure 4:
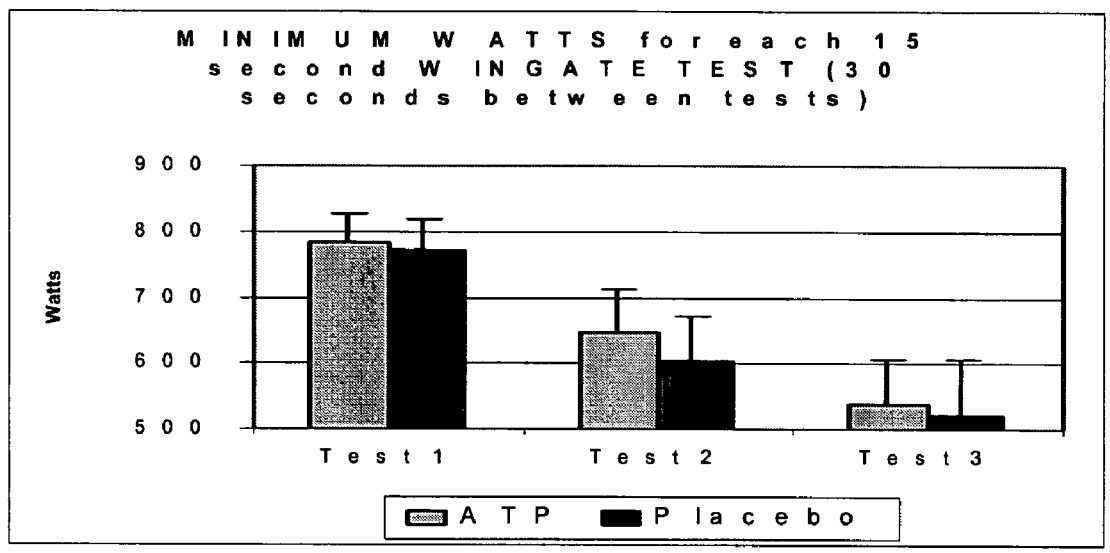
FIG. 4 is a graph illustrating the difference in minimum watts between placebo and one presently preferred embodiment of an ATP composition of the present invention for three (3) successive Wingate tests.

As shown in FIG. 4, a bar graph illustrates one presently preferred embodiment of a level of minimum muscle output during the entire 15 second test for each of the three (3) back-to-back tests following administration of the ATP composition of the present invention versus placebo.

Figure 5:
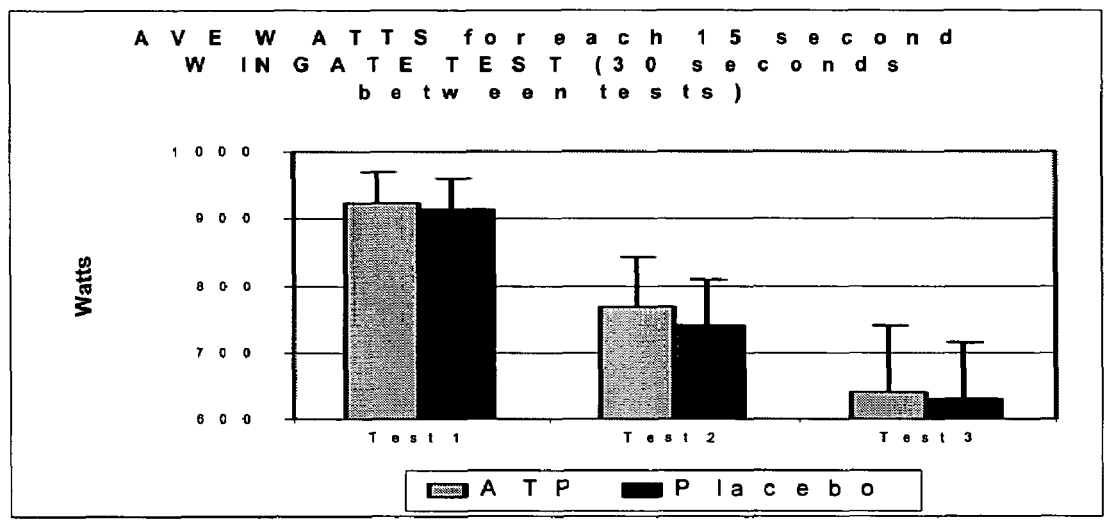
FIG. 5 is a graph illustrating the average watts between placebo and one presently preferred embodiment of an ATP composition of the present invention for three (3) successive Wingate tests.

Referring now to FIG. 5, a bar graph shows one presently preferred embodiment of a level of average muscle output during the entire 15 second test for each of the three (3) back-to-back tests following administration of the ATP composition of the present invention versus placebo.

Figure 6:
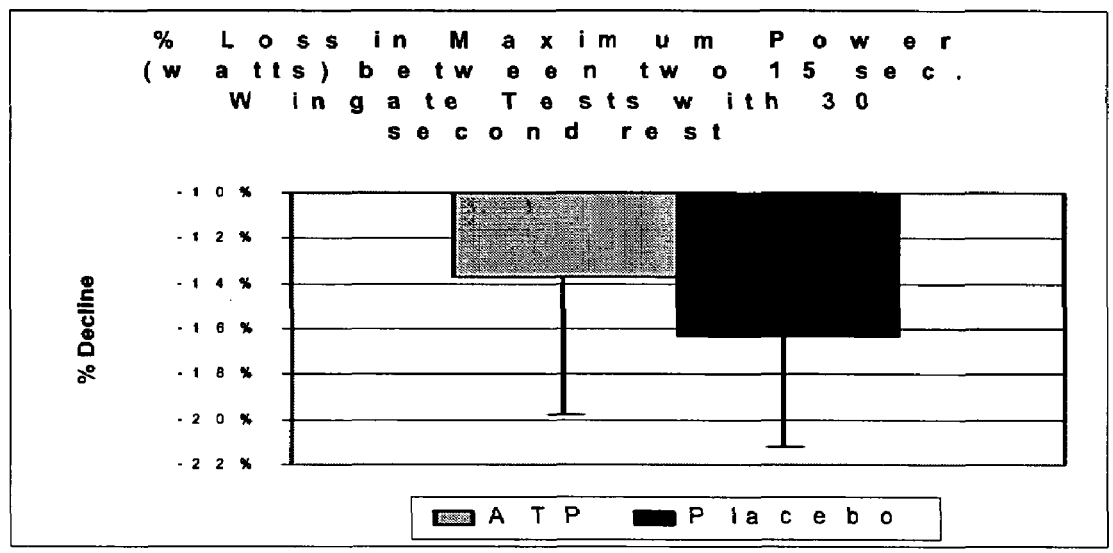
FIG. 6 is a graph illustrating the percentage loss in maximum power between placebo and one presently preferred embodiment of an ATP composition of the present invention during a thirty (30) second Wingate test.

Referring now to FIG. 6, a bar graph illustrates one presently preferred embodiment of a decrease in maximum muscle output between the first (1st) and second (2nd) Wingate test following administration of the ATP composition of the present invention versus placebo.

Figure 7:
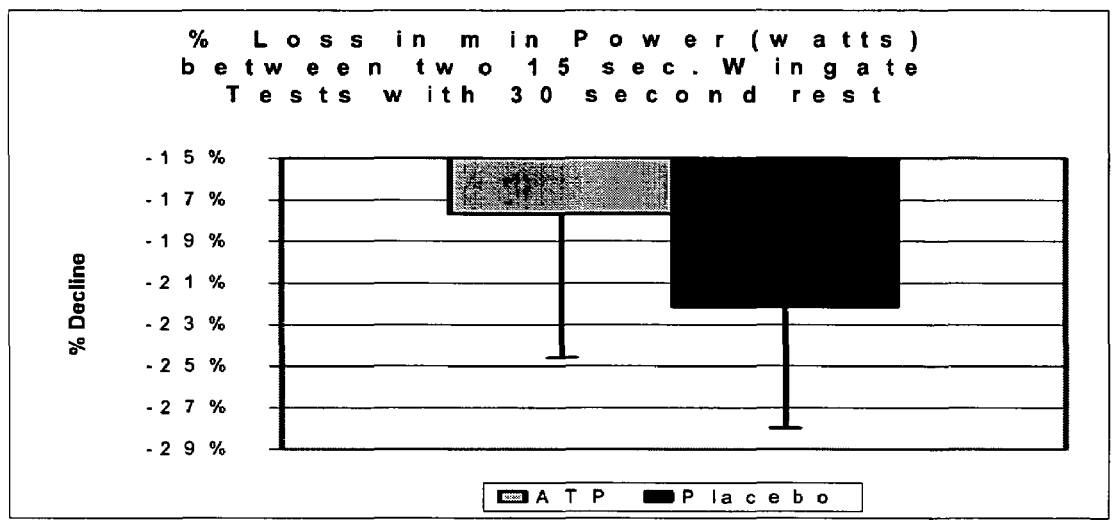
FIG. 7 is a graph illustrating the percentage loss in maximum power between placebo and one presently preferred embodiment of an ATP composition of the present invention during a fifteen (15) second Wingate test.

As shown in FIG. 7, a bar graph shows one presently preferred embodiment of a decrease in minimum muscle output between the first (1 st) and second (2nd) Wingate test following administration of the ATP composition of the present invention versus placebo.

Figure 8:
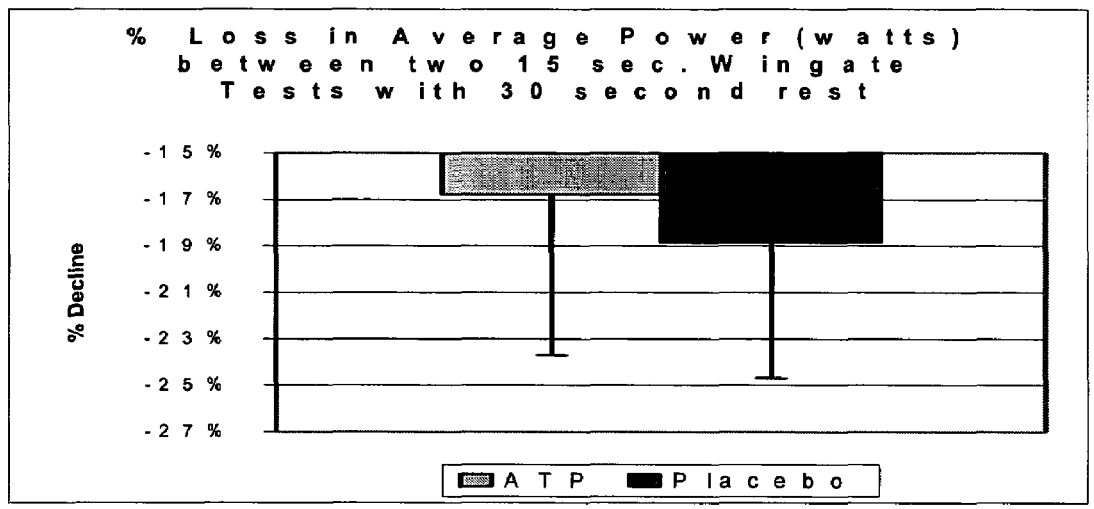
FIG. 8 is a graph illustrating the percentage loss in average power between placebo and one presently preferred embodiment of an ATP composition of the present invention during a thirty (30) second Wingate test.

Referring now to FIG. 8, a bar graph illustrates one presently preferred embodiment of a decrease in average muscle output between the first (1st) and second (2nd) Wingate test following administration of the ATP composition of the present invention versus placebo.

EXAMPLE IV

In yet another presently preferred embodiment of a method for preparing an ATP composition of the present invention, Adenosine-5'-Triphosphate Disodium may be agglomerated into granules using a seed crystal nucleus upon which a mixture containing ATP and various excipients for binding and flow are progressively loaded using a fluidized bed processor. The base granulation formula of one presently preferred embodiment may include the following, for example and not by way of limitation:
   20% ATP
   20% Microcrystalline Cellulose
   20% Starch
   35% Sucrose
   5% Maltodextrin The resulting agglomeration prepared as outlined above may then be dried with a loss of weight on drying of about one percent (1%) to about four percent (4%), and yielding a granule from about 100 microns to about 1000 microns in size with an active ATP "drug" load of approximately ten percent (10%) to about thirty percent (30%). The loaded particles may then be coated with about fifteen percent (15%) to about forty percent (40%) aqueous enteric coating containing approximately sixty-three percent (63%) (Emcoat 120N )), aboutl 9.5% Hydroxypropylmethylcellulose (HPMC), about 12.5% Oleic acid and about 5% Triacetin. In one presently preferred embodiment, the prepared granules may be encapsulated in two (2)-piece hard gelatin capsules using microcrystalline cellulose as a filler and less than three percent (3%) magnesium stearate as a lubricant.

EXAMPLE V

Using the same tablet preparation of one presently preferred embodiment of the ATP composition of the present invention consumed in Examples II and III, another test was conducted to evaluate the bioavailability (i.e., the degree and rate at which a substance may be absorbed into a living system or otherwise made available at a site of physiological activity) of a single dose (containing an average about 850 mg ATP) of the ATP composition of the present invention. The tablets containing the ATP composition of the present invention were given to two volunteers for the purpose of evaluating relative changes in intracellular and extracellular ATP levels following the dosage. The dosage was administered on an empty stomach, whereby the volunteers had fasted from midnight until the test, about eight (8) hours later. One volunteer received a dose of about 15 mg active ATP/kg and the second volunteer received a dose of about 7.5 mg active ATP/kg.

Figure 9:
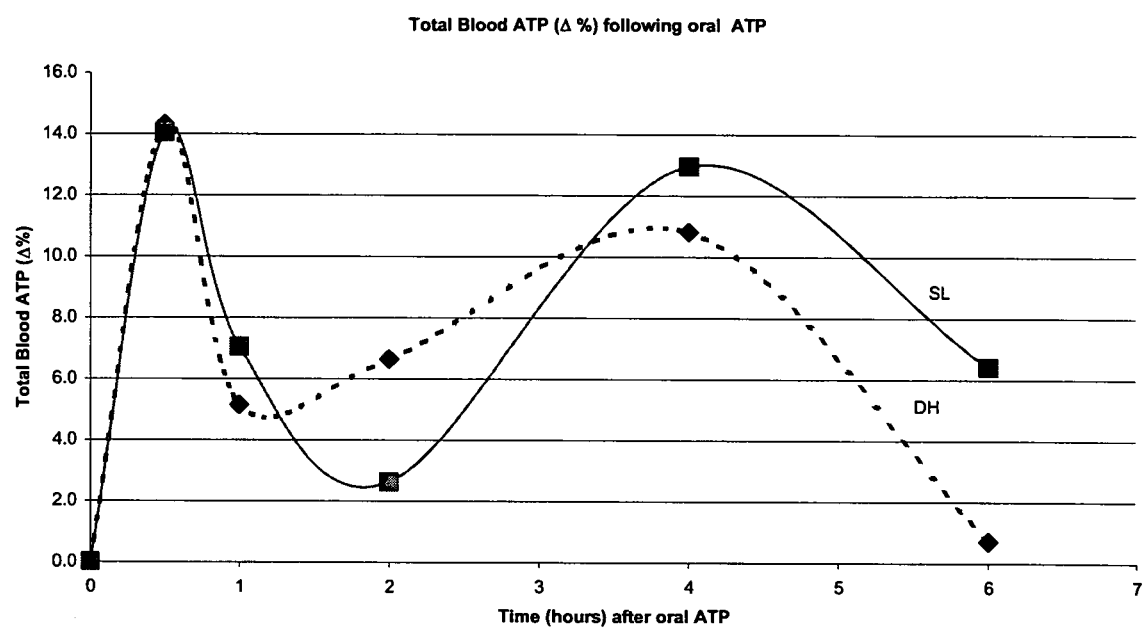
FIG. 9 is a graph illustrating an example of one presently preferred embodiment of a percentage change in total blood ATP in two human subjects over six (6) hours.
Figure 10:
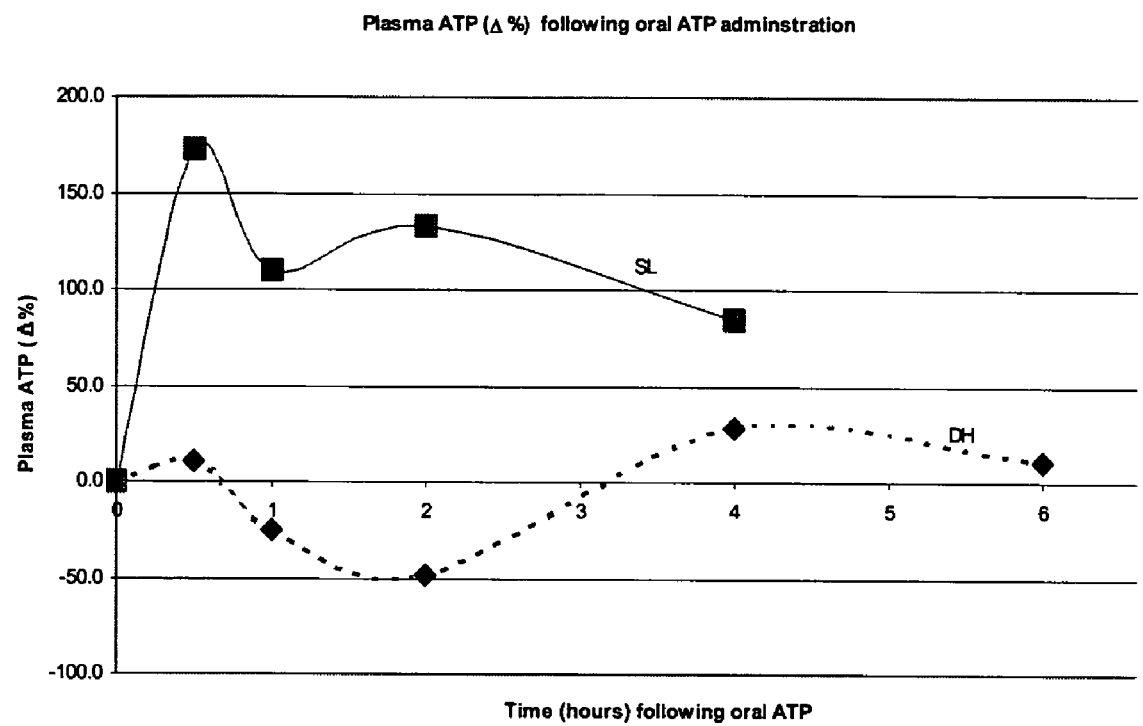
FIG. 10 is a graph illustrating an example of one presently preferred embodiment of a percentage change in plasma ATP in two human subjects over six (6) hours.

A baseline blood ATP level was obtained immediately prior to dosage administration and additional ATP blood levels were obtained at intervals of thirty (30) minutes, one (1) hour, two (2) hours, four (4) hours, and six (6) hours following dosage administration. Referring now to FIGS. 9 and 10, the results of this test are illustrated.

Referring specifically to FIG. 9, a graph is provided which illustrates the results of an example of one presently preferred embodiment of a percentage change of the concentration of ATP in total blood in two human subjects over six (6) hours following dosage administration. Referring now to FIG. 10, a graph is provided which illustrates the results of an example of one presently preferred embodiment of a percentage change in concentration of ATP in plasma in two human subjects over six (6) hours following dosage administration.

The experiment outlined in the present Example specifically sought to measure the presence of a pharmacokinetic dose-response within the intracellular and extracellular body compartments following the administration of a single dosage of a presently preferred embodiment of the ATP composition of the present invention.

FIGS. 9 and 10 demonstrate that there is a measurable relationship between the oral administration of an effective amount of the ATP compositions of the present invention and alterations in blood and plasma concentrations of ATP in the body of the participants. Moreover, FIGS. 1 through 8 demonstrate a measurable relationship between the oral administration of an effective amount of the ATP compositions of the present invention and human physical performance testing. These data show that the compositions of the present invention provide a method for effecting intracellular and extracellular ATP concentrations and increasing human performance by reducing muscle fatigue and recovery time which comprises administering an effective amount of ATP to a human in need of such treatment.

EXAMPLE VI

Increasing Anaerobic Capacity

There has been significant interest in the conception and development of ergogenic substances over at least the past twenty years. For example, creatine monohydrate has enjoyed much popularity as an aid to short duration, high-intensity exercise performance, sometimes referred to as anaerobic exercise.

In search of additional ergogenic substances, those skilled in the art may appreciated that ATP may play an important role in muscle function. However, the full range of ATP effects on the muscle and body have remained unknown. For example, ATP is known to be involved in neurotransmission, cardiac function, and in platelet function (e.g., blood clotting). Difficulties in effective delivery of ATP during exercise, however, may have hindered and/or prevented previous investigation of ATP effects.

In the midst of anaerobic exercise, the muscles and other organs of the body may depend upon ATP, glycogen, and phosphocreatine to supply the energy to continue biochemical reactions. As appreciated, ATP, glycogen, and phosphocreatine may not be stored in significant amounts by the body. Therefore novel systems and methods for effectively supplementing the body's stores of ATP may be helpful in meeting demands of anaerobic exercise. A study was conducted to evaluate the effect of one presently preferred embodiment of an ATP composition of the present invention on anaerobic exercise performance values, which is outlined as follows:

Study Inclusion Criteria:

Thirty healthy males were recruited to participate in a trial at The Cooper Institute (Dallas, Tex.) for a series of three high-intensity anaerobic power assessments. Participation inclusion criteria included: (1) male gender; (2) age between eighteen and forty-five years; (3) at least a six month creatine free interval prior to the study; and (4) current involvement in a strength training program (i.e., two to four times a week for at least twelve months). Participants were asked to refrain from any vigorous physical activity for twenty-four hours prior to assessment and asked to fast for at least 3 hours prior to assessment. Twenty-seven participants completed the study.

Study Design:

Anaerobic exercise performance were evaluated on three separate occasions via the completion of two Wingate tests. The occasions for evaluation preferably occurred at a baseline evaluation period, an acute evaluation period (i.e., seven days following baseline, one hour following initial ATP composition or placebo administration), and after fourteen days of supplementation with ATP composition or placebo. Wingate tests were performed on a Lode Excalibur Sport Cycle Ergometer (Groningen, Netherlands). During each testing period, all subjects reported to the testing lab at the same time of day for each successive measurement.

Each subject was allowed to warm up for a period of approximately fifteen minutes on the testing ergometer. More specifically, the warm-up period may include ten minutes of general steady state pedaling, followed by five minutes of intermittent short sprinting pedaling. Each Wingate test began with a thirty second period of unload pedaling. Each subject was instructed to begin pedaling at a slow, self-selected pace. A subject was provided with a verbal countdown at the ten second mark to give the subject sufficient time to achieve maximum pedal cadence by the beginning of the test.

Following the countdown period, tension may be automatically added to the ergometer and each subject may pedal as fast as possible for thirty seconds against a flywheel resistance set at 0.08 mg per kg of body mass. Verbal encouragement to the subject may be continued throughout the test. Each subject may complete two. Wingate tests separated by five minutes of rest. The same flywheel resistance may be used for each Wingate test.

Each subject was also be evaluated for blood lactate accumulation at three minutes following each Wingate test. A whole blood sample was evaluated for lactic acid using an Analox GM7 Micro-Stat Lactate Analyzer™ (London, UK). Whole blood lactic acid was obtained from each subject using a finger stick (i.e., puncture) procedure and collection in capillary tubes which contained heparin, fluoride, and nitrite. Fluoride may be used as a glycolysis inhibitor and nitrite may be used to convert hemoglobin to the methemoglobin form to prevent uptake or egress of oxygen from the sample. The analysis of the blood sample was performed within two to three minutes of sample collection.

In addition, before each of the acute and post testing assessment periods, a 2.5 mL blood sample was collected through venipuncture and transferred to a vacutainer containing ethylenediaminetetracetic acid potassium salt (EDTA $K_3$) solution (Vacutainer, Becton Dickinson Company, Franklin Lakes, N.J.). Shear stress to the sample was minimized by releasing the vacuum prior to sample collection.

Immediately following sample collection, 1 mL of blood was transferred from the EDTA $K_3$ solution tube into a 1.5 mL Eppendorf tube with 0.2 mL of polymer separtor gel and centrifuged for two to three minutes at 6000×g at 4° C. A firefly luciferase assay was performed by a 12-detector luminometer (Perkin-Elmer Bioscienc, Boston, Mass.) on the blood sample to determine ATP concentrations which may be down to the subnanomolar concentration range.

As appreciated by those skilled in the art, numerous sample collection and analysis techniques may be available to evaluate the blood lactate accumulation. Accordingly, the collection and analysis techniques set forth in the present Example are merely exemplary of one present preferred embodiment of the present invention and is not intended to limiting of the breadth and scope of the methodologies of the present invention.

Primary outcome variables from the Wingate tests included peak anaerobic power, which may be characterized as: (i) the greatest output (i.e., peak output—"PO") in power (i.e., "W") achieved during the test; (ii) the total amount of work exhibited during the entire thirty second testing period; and (iii) the average PO produced during the thirty second testing period. The total work produced for each ten second period of the test (i.e., 0-10 seconds, 11-20 seconds, and 21-30 seconds, respectively) were also observed and evaluated.

Each subject participant was examined on three separate occasions, as follows: (I) baseline; (ii) acutely (i.e., seven days after baseline and seventy-five minutes following ATP administration); and (iii) after fourteen days of ATP administration (i.e., twenty-one days following baseline).

Following baseline testing, each subject was assigned, in a randomized, double-blind fashion, to receive either a high dose (i.e., 225 mg) of enterically coated ATP, a low dose (i.e., 150 mg) of enterically coated ATP, or a visibly similar placebo. Seven days following the baseline test, each subject returned to the lab to undergo an acute dose evaluation phase. Supplementation with ATP or placebo began seventy-five minutes prior to the acute test and continued for fourteen days of supplementation.

As appreciated in the art, ATP may be coated to improve delivery, administration and/or bioavailability. Coated ATP may have protection against decomposition by acid in the gastrointestinal system. In addition, coated ATP may lead to improved absorption of ATP into the systemic circulation.

Results:

Referring now to FIG. 11, the results of the blood ATP concentrations are illustrated in table form. As noted from reviewing the results set forth in the table, there was no statistically significant difference in the blood sample measured parameters. While animal trials have previously shown significant results in the absorption of purine nucleotides (e.g., ATP) and accumulation in the bloodstream, that significant change was not apparent in this study. However, transient increases in ATP concentration may be suggestive that there is some transport beyond the portal system. The relatively larger size for the ATP molecule may be at least partly responsible for this observation. It is possible that other delivery systems, alone or in combination with enteric-coated systems, may provide a greater ATP blood concentration.

Referring now to FIG. 12, the results of the Wingate tests and blood lactic acid concentration are illustrated in table form. As noted from reviewing the results set forth in the table, there were no significant changes between the baseline, acute, and post-treatment phases of the evaluation period.

EXAMPLE VII

Increasing Muscular Mass and/or Strength

Another aspect of anaerobic performance may be muscle mass and/or muscular strength. Strength conditioning training and research has been the subject of significant interest in the conception and development of ergogenic substances. As with other tests of anaerobic capacity, creatine monohydrate has become popular as an aid to building muscle mass and/or strength.

It has been found that the use of ATP during a muscle strength and condition program results in greater stores of ATP and thus greater capacity for building muscle strength. Therefore, novel systems and methods for effectively supplementing the body's stores of ATP may be helpful in meeting demands of anaerobic exercise. A study was conducted to evaluate the effect of one presently preferred embodiment of an ATP composition of the present invention on anaerobic exercise performance values, which is outlined as follows:.

Study Inclusion Criteria:

Thirty healthy males were recruited to participate in a trial study at The Cooper Institute (Dallas, Tex.) for a series of three high-intensity anaerobic power assessments. Participation inclusion criteria included: (1) male gender; (2) age between eighteen and forty-five years; (3) at least a six month creatine free interval prior to the study; and (4) current involvement in a strength training program (i.e., two to four times a week for at least twelve months). Participants were asked to refrain from any vigorous physical activity for twenty-four hours prior to assessment and asked to fast for at least three hours prior to assessment. Twenty-seven participants completed the study.

Study Design:

Increase in muscle mass and/or strength were evaluated on three separate occasions via the completion of a 1-repetition maximum (RM) bench press test, and three sets of repetitions to fatigue at seventy percent (70%) of 1RM. The occasions for evaluation occurred at a baseline evaluation period, an acute evaluation period (i.e., seven days following baseline and one hour following initial ATP composition or placebo administration), and after fourteen days of supplementation with ATP composition or placebo. 1-RM bench press tests and repetitions to fatigue were performed on a Universal bench press machine with dynamic variable resistance. Test reliability of the 1RM test has been shown to be highly correlated over a period of nine days.

Five minutes after completing a 1RM test, each subject completed three sets of repetitions to fatigue, with two minutes between each set. For each subject and at each evaluation session (i.e., baseline, acute, post-fourteen days supplementation), the 1RM value (kg), the 70% 1RM value (kg), and the number of repetitions for each set were recorded. In addition a total lifting volume (TLV; in kg) may be calculated with the following equation:

$$TLV = [70\% \ 1RM \times \text{set 1 reps}] + [70\% \ 1RM \times \text{set 2 reps}] + [70\% \ 1RM \times \text{set 3 reps}]$$

During each testing period (i.e., evaluation session), all subject participants reported to the testing lab at the same time of day for each successive measurement.

Results:

Referring now to FIG. 13, the results of the strength testing study outlined hereinabove are described in the table. There was one statistically significant difference and there were several within group statistical differences, especially in the group receiving high dose ATP. In the 1RM bench press test, those receiving the high dose ATP composition had a significant increase at the acute evaluation period compared to the baseline measurements. In addition, the TLV for those in the high dose group increased after fourteen days of supplementation compared to the baseline values. Moreover, the high dose ATP group experienced an increase in the set 1 repetitions to fatigue. The change in individual and group mean data for 1-RM bench press testing is set forth in the table illustrated in FIG. 14.

In addition to the above-identified results, those in the high dose ATP group also reported an improved sense of well-being during their participation in the study. This effect may be due to the role of ATP as a neurotransmitter and/or pain perception modifying agent. Previous research may suggest the possibility of ATP and similar nucleotides in the alteration of central nervous system responses. In particular, these effects may be mediated through the noradrenaline, glutamine, and serotonin neurotransmitter systems. Moreover, pain modifying effects may be accomplished through the stimulation of Adenosine receptors (e.g., sub-type 1 and sub-type 2).

EXAMPLE VIII

Increases in Perfusion Pressure, Oximetry, and Erythrocyte ATP Concentration

Preferred embodiments of the present invention may be used at dosages of between about 7 mg ATP/kg body weight and about 14 mg ATP/kg body weight to evaluate the effects on perfusion pressure, oximetry, and erythrocyte ATP concentration in human subjects. As appreciated, ATP effectively increases the body's extracellular levels of ATP. The normal aging process in humans and animals and stress on the body are known to reduce extracellular ATP levels.

Following ingestion, preferred embodiments of the ATP compositions of the present invention may be broken down in the small intestine into free adenosine and free phosphate components. These components may be rapidly absorbed and subsequently absorbed into liver cells and red blood cells to expand ATP pools. Red blood cell (RBC) ATP pools may be slowly released into the blood plasma and this supplemental ATP activates specialized ATP receptors on the surface of vascular endothelial cells. The activation of endothelial cells may result in improved blood vessel tone and relaxation of the vessel walls so that more blood may be able to move through the vessels to the heart, lungs, brain, and peripheral vasculature, as well as other organs.

Figure 15:
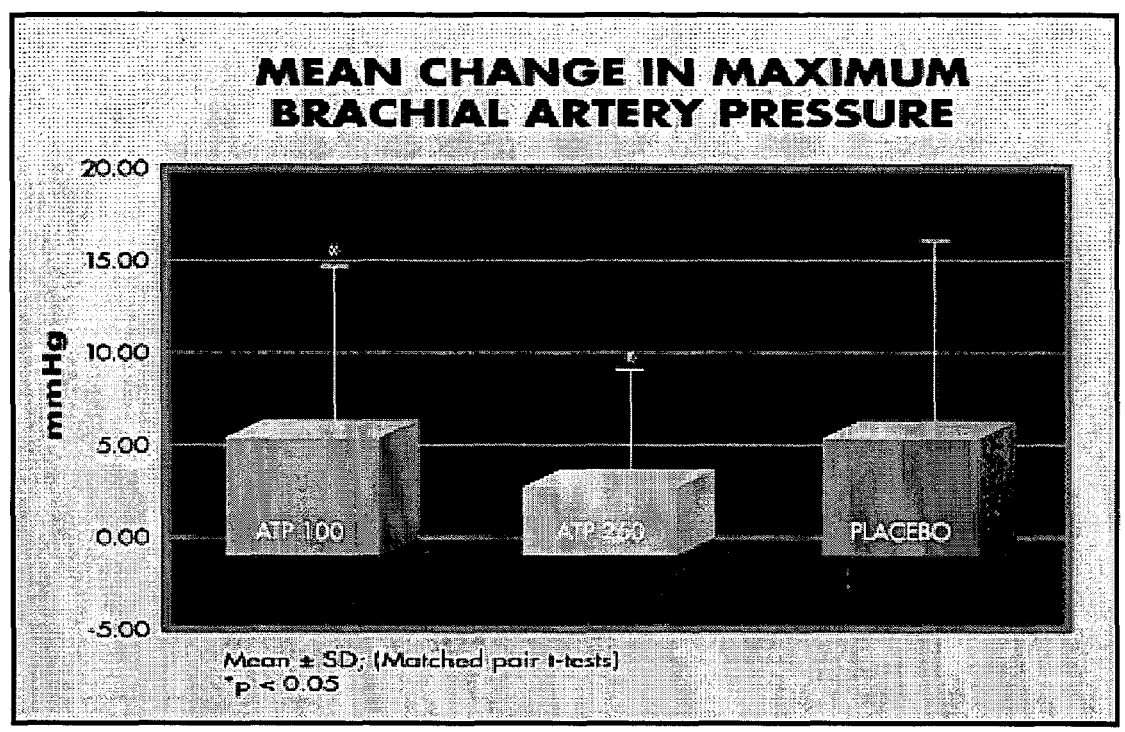
FIG. 15 is a graph is provided which illustrates the results of an example of one presently preferred embodiment of mean change in maximum brachial artery pressure following administration of one presently preferred embodiment of an ATP composition of the present invention.

Referring now to FIG. 15, a graph is provided which illustrates the results of an example of one presently preferred embodiment of mean change in maximum brachial artery pressure (i.e., in the upper extremity) following administration of one presently preferred embodiment of an ATP composition of the present invention. These increases in maximum brachial artery pressure did not adversely affect heart rate or blood pressure. Moreover, increases in organ perfusion may result in enhanced delivery of glucose, nutrients, and oxygen to peripheral sites. Increases in organ perfusion may also result in more efficient removal of catabolic waste products from organs and other tissues in the body.

Figure 16:
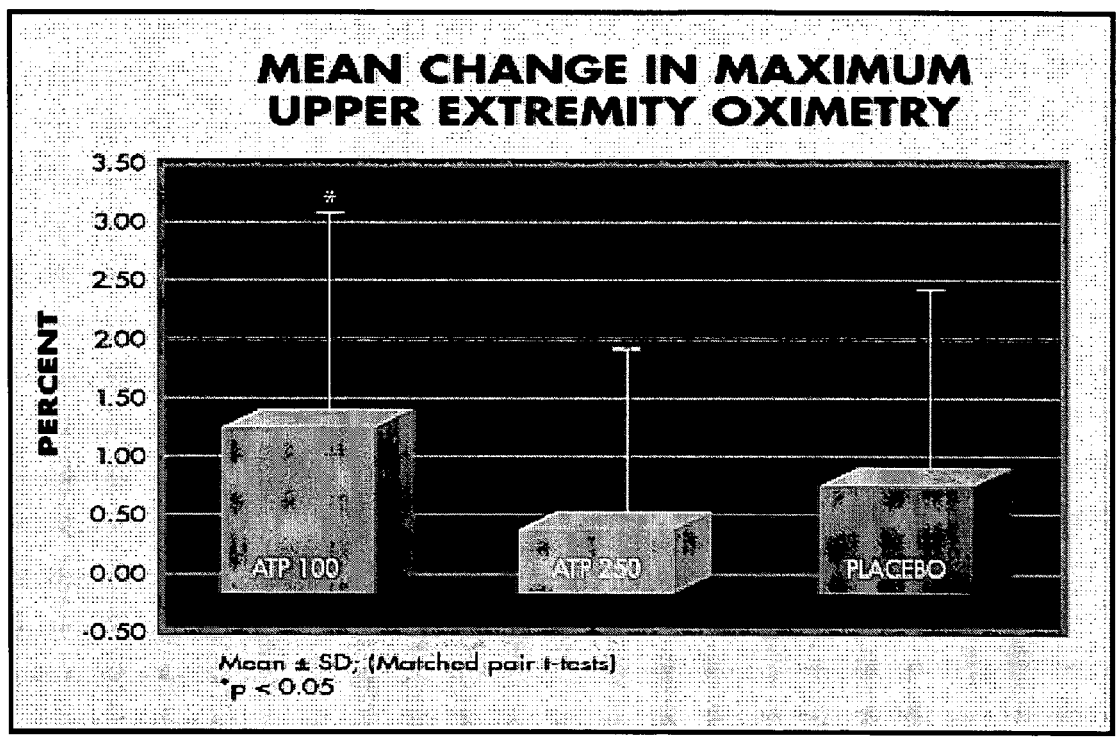
FIG. 16 is a graph which illustrates the results of an example of one presently preferred embodiment of mean change in maximum upper extremity oximetry following administration of one presently preferred embodiment of an ATP composition of the present invention in human subjects.

As shown in FIG. 16, a graph is provided which illustrates the results of an example of one presently preferred embodiment of mean change in maximum upper extremity oximetry (i.e., degree of oxygen saturation in the circulating blood) following administration of one presently preferred embodiment of an ATP composition of the present invention in human subjects. When oxygen saturation is low in the body, RBCs may act as sensors and signal for the release of additional ATP into the bloodstream. This may result in multiple physiological effects. For example, and not by limitation, regulation of vascular tone to reduce pulmonary and systemic vascular resistance without adversely affecting blood pressure or heart rate may stimulate blood flow. Enhanced perfusion to the heart, lungs, brain, and other tissues may promote a more active lifestyle, boost mental acuity, improve muscle mass and function, improve physical performance, lessen perception of exercise-induced pain, and may relieve cold hands and feet.

Figure 17:
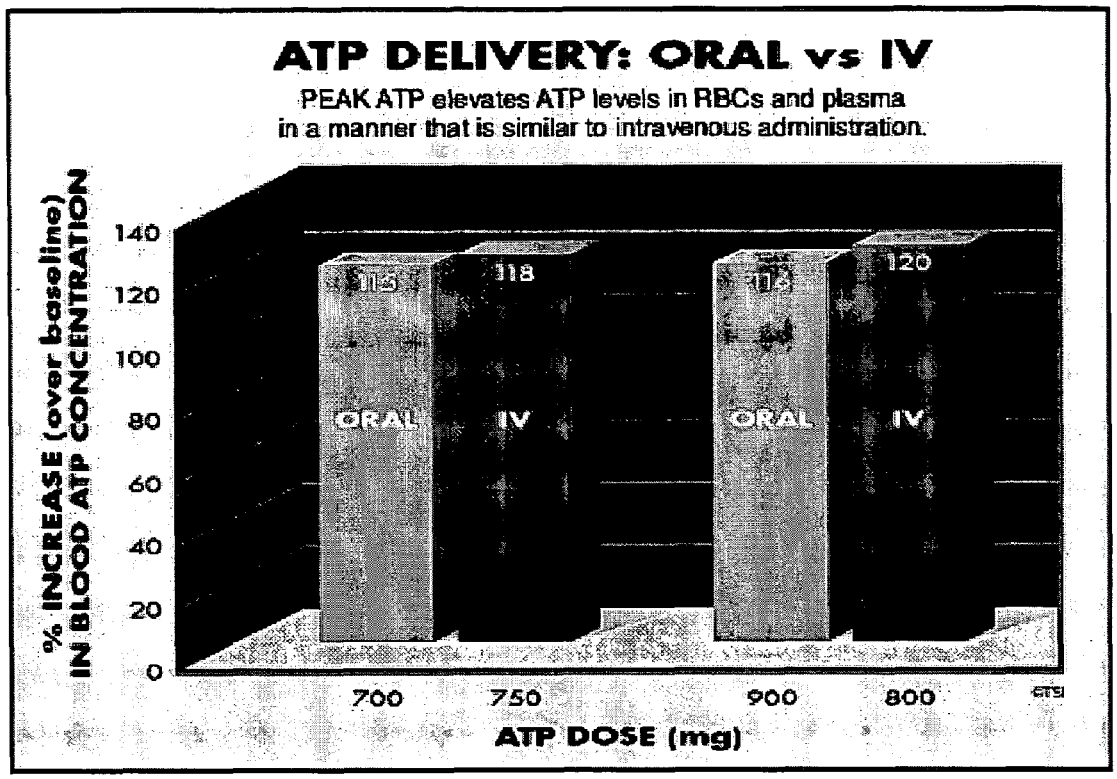
FIG. 17 is a graph that illustrates that presently preferred embodiments of the ATP compositions of the present invention administered in an oral formulation achieve increases in blood ATP concentration (i. e., RBC ATP concentrations) that are consistent with increases achieved by intravenous formulations of ATP.

Referring now to FIG. 17, a graph is provided that illustrates that presently preferred embodiments of the ATP compositions of the present invention administered in an oral formulation may achieve increases in blood ATP concentration (i.e., RBC ATP concentrations) that are consistent with increases achieved by intravenous formulations of ATP. In contrast, numerous prior art methods and compositions have taught that ATP may not be absorbed in sufficient quantities to achieve these concentrations. The present example, however, demonstrates sufficient intracellular ATP levels may be achieved.

Figure 18:
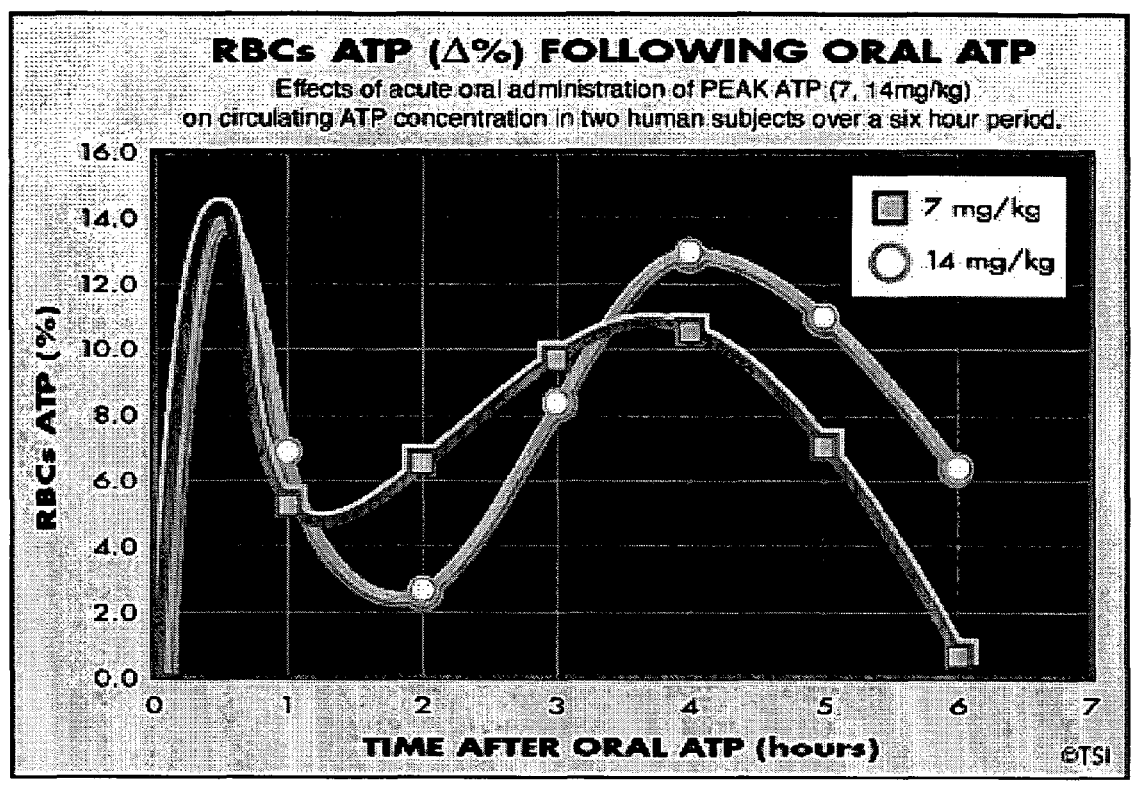
FIG. 18 shows a graph that illustrates one presently preferred embodiment of the effects on RBC ATP concentration following oral administration of a presently preferred embodiment of the ATP compositions of the present invention in human subjects.

As shown in FIG. 18, a graph is provided that illustrates one presently preferred embodiment of the effects on RBC ATP concentration following oral administration of a presently preferred embodiment of the ATP compositions of the present invention at dosages of 7 mg/kg and 14 mg/kg in human subjects.

In summary, the Examples disclosed herein demonstrate that the ATP compositions of the present invention provide a method for effecting intracellular and extracellular ATP concentrations in mammals. Additionally, the present invention substantially increases human performance by increasing endurance and muscle output through reduction in muscle fatigue and decrease in muscle recovery time after exhaustion. Moreover, the present invention provides systems and methods for delivering oral administration of ATP in a manner that protects it from degradation by gastric juices through enteric coating to enhance absorption into the blood stream or through avoiding exposure to gastric juices by sublingual administration, and provide additional therapeutic benefit when compared with non-protected forms.

The Examples outlined herein further illustrate systems and methods for enterically coating ATP compatible with manufacture of foods, drugs, and dietary supplements of complex formulation and various dosage forms without the need for imparting enteric properties to the entire mixture, any other part of the mixture, or finished products.

In addition, the Examples disclosed herein illustrate systems and methods for using enterically coated ATP for increasing anaerobic capacity, increasing muscle mass and/or strength, increasing organ perfusion, and increasing erythrocyte ATP concentrations. These properties may translate into declining the aging process, and/or enhancing energy, vitality, longevity, and athletic performance. The results represented in FIGS. 1 through 18 are statistically accurate.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. A method of increasing muscle strength in a mammal comprising the steps of administering to said mammal an effective amount of Adenosine Triphosphate ("ATP") to increase muscle strength of muscles of the mammal while said mammal is participating in a strength training program.

2. The method of claim 1, wherein the method further increases muscle mass of the mammal.

3. The method of claim 1, wherein the method further increases total lifting volume of muscles of the mammal participating in a strength training program.

4. The method of claim 1, wherein the effective amount of ATP is between about 150 mg and about 850 mg.

5. The method of claim 1, wherein the effective amount of ATP is between about 7.5 mg ATP/kg body weight and about 14 mg ATP/kg body weight of the mammal.

6. The method of claim 1, wherein the step of administering is selected from the group consisting of oral, parenteral, sublingual, topical, transdermal, intramuscular, and inhalation.

7. The method of claim 6, wherein the oral administration comprises a delivery form selected from the group consisting of tablet, capsule, powder, granule, microgranule, pellet, soft-gel, controlled-release form, liquid, solution, elixir, syrup, suspension, emulsion, and magma.

8. The method of claim 1, further comprising the step of introducing the effective amount of ATP into a functional food form.

9. The method of claim 1, wherein the effective amount of ATP is combined with one or more compounds selected from the group consisting of amino acids, proteins, carbohydrates, botanicals, and herbals.

10. The method of claim 1, wherein the effective amount of ATP is combined with branched-chain amino acids.

11. A method of increasing muscle mass in a mammal comprising the steps of administering to said mammal an effective amount of Adenosine Triphosphate ("ATP") to a mammal to increase muscle mass of the muscles while said mammal is participating in a strength training program.

12. The method of claim 11, wherein the method further increases total lifting volume of the muscles of the mammal.

13. The method of claim 11, wherein the effective amount of ATP is between about 150 mg and about 850 mg.

14. The method of claim 11, wherein the effective amount of ATP is between about 7.5 mg ATP/kg body weight and about 14 mg ATP/kg body weight of the mammal.

15. The method of claim 11, wherein the step of administering is selected from the group consisting of oral, parenteral, sublingual, topical, transdermal, intramuscular, and inhalation.

16. The method of claim 11, wherein the oral administration comprises a delivery form selected from the group consisting of tablet, capsule, powder, granule, microgranule, pellet, soft-gel, controlled-release form, liquid, solution, elixir, syrup, suspension, emulsion, and magma.

17. The method of claim 11, wherein the effective amount of ATP is combined with one or more compounds selected from the group consisting of amino acids, proteins, carbohydrates, botanicals, and herbals.

18. The method of claim 11, wherein the effective amount of ATP is combined with branched-chain amino acids.

19. The method of claim 11, further comprising the step of introducing the effective amount of ATP into a functional food form.

20. The method of claim 1 further comprising administering an effective amount of Adenosine Triphosphate ("ATP") and at least one amino acid, other than ATP, to said mammal.

21. The method of claim 20, wherein the at least one amino acid comprises a branched-chain amino acid.

22. The method of claim 20, wherein the at least one amino acid comprises arginine.

23. The method of claim 20, wherein the amount of ATP is between about 7.5 mg ATP/kg body weight and about 14 mg ATP/kg body weight of the mammal.

24. The method of claim 11 further comprising administering an effective amount of Adenosine Triphosphate ("ATP") and at least one amino acid, other than ATP, to said mammal.

25. The method of claim 11, wherein the at least one amino acid comprises a branched-chain amino acid.

26. The method of claim 11, wherein the at least one amino acid comprises arginine.

27. The method of claim 11, wherein the amount of ATP is between about 7.5 mg ATP/kg body weight and about 14 mg ATP/kg body weight of the mammal.

* * * * *

UNITED STATES PATENT AND TRADEMARK OFFICE
CERTIFICATE OF CORRECTION

| | | |
|---|---|---|
| PATENT NO. | : 7,629,329 B2 | Page 1 of 1 |
| APPLICATION NO. | : 11/069746 | |
| DATED | : December 8, 2009 | |
| INVENTOR(S) | : Lee et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1082 days.

Signed and Sealed this

Second Day of November, 2010

David J. Kappos
*Director of the United States Patent and Trademark Office*